US011497464B2

(12) United States Patent
Megens et al.

(10) Patent No.: US 11,497,464 B2
(45) Date of Patent: **\*Nov. 15, 2022**

(54) MEDICAL ULTRASOUND DEVICE WITH TEMPERATURE DETECTION AT DISTAL END

(71) Applicant: KONINKLIJKE PHILIPS N.V., Eindhoven (NL)

(72) Inventors: Mischa Megens, Utrecht (NL); Jan Frederik Suijver, Dommelen (NL)

(73) Assignee: KONINKLIJKE PHILIPS N.V., Eindhoven (NL)

( \* ) Notice: Subject to any disclaimer, the term of this patent is extended or adjusted under 35 U.S.C. 154(b) by 151 days.

This patent is subject to a terminal disclaimer.

(21) Appl. No.: 16/996,466

(22) Filed: Aug. 18, 2020

(65) Prior Publication Data

US 2020/0375569 A1 Dec. 3, 2020

Related U.S. Application Data

(63) Continuation of application No. 13/393,857, filed as application No. PCT/IB2010/054143 on Sep. 15, 2010, now Pat. No. 10,743,836.

(30) Foreign Application Priority Data

Sep. 17, 2009 (EP) ..................... 09170526

(51) Int. Cl.
| | |
|---|---|
| *A61B 8/00* | (2006.01) |
| *A61B 8/08* | (2006.01) |
| *G01K 11/24* | (2006.01) |
| *A61B 18/14* | (2006.01) |
| *A61B 8/12* | (2006.01) |

(Continued)

(52) U.S. Cl.
CPC .................. *A61B 8/08* (2013.01); *A61B 8/12* (2013.01); *A61B 8/445* (2013.01); *A61B 8/4483* (2013.01);

(Continued)

(58) Field of Classification Search
CPC ....... A61B 8/445; A61B 8/4483; A61B 8/546; A61B 2018/00791; G01K 2217/00
See application file for complete search history.

(56) References Cited

U.S. PATENT DOCUMENTS

| | | |
|---|---|---|
| 5,196,006 A | 3/1993 | Klopotek |
| 6,490,474 B1 | 12/2002 | Parker |

(Continued)

FOREIGN PATENT DOCUMENTS

| | | |
|---|---|---|
| CN | 101283925 A | 10/2008 |
| CN | 101396299 A | 4/2009 |
| JP | 10127632 | 5/1998 |

OTHER PUBLICATIONS

Therapy Dual-8 Ablation Catheter, URL: http://www.sjmprofessional.com/Products/Intl/Ablation-Therapy/Therapy-Dual-8-Ablation-Catheter.aspx. Accurate Temperature Sensor at Tip of Integrated Ablation and Monitoring Catheter.

(Continued)

*Primary Examiner* — Rochelle D Turchen (57) ABSTRACT

A medical ultrasound device is disclosed. The device comprises an elongated body having a proximal end, a distal end (10) and a distal end region (1). One or more ultrasound transducers (4) for generating acoustic radiation are positioned in the distal end region, inside the elongated body. A transmission element (5) which is substantially transparent to acoustic radiation is positioned in the radiation path of the acoustic radiation, and a controller unit is operatively connected to the ultrasound transducer. The controller unit detects the acoustic path length through the transmission element and determines the temperature at the distal end from the detected acoustic path length. In an embodiment, the medical device is an ultrasound RF ablation catheter.

14 Claims, 5 Drawing Sheets

(51) Int. Cl.
*G01K 13/20* (2021.01)
*A61B 18/00* (2006.01)
*A61N 7/00* (2006.01)
*A61B 18/12* (2006.01)
*A61B 90/00* (2016.01)

(52) U.S. Cl.
CPC .......... *A61B 8/546* (2013.01); *A61B 18/1492* (2013.01); *G01K 11/24* (2013.01); *G01K 13/20* (2021.01); *A61B 8/0883* (2013.01); *A61B 18/1206* (2013.01); *A61B 2018/00702* (2013.01); *A61B 2018/00791* (2013.01); *A61B 2090/3782* (2016.02); *A61N 2007/0078* (2013.01); *G01K 2217/00* (2013.01)

(56) References Cited

U.S. PATENT DOCUMENTS

| | | |
|---|---|---|
| 6,656,136 B1 | 12/2003 | Weng |
| 6,788,967 B2 | 9/2004 | Ben-Haim |
| 7,438,684 B2 | 10/2008 | Fujii |
| 9,844,443 B2 | 12/2017 | Puno |
| 2003/0078498 A1 | 4/2003 | Lang |
| 2003/0130657 A1 | 7/2003 | Tom |
| 2004/0078036 A1 | 4/2004 | Keidar |
| 2004/0127791 A1 | 7/2004 | Mast |
| 2004/0236223 A1 | 11/2004 | Barnes |
| 2004/0258127 A1 | 12/2004 | Ramamurthy |
| 2005/0080334 A1 | 4/2005 | Willis |
| 2006/0030844 A1 | 2/2006 | Knight |
| 2006/0184069 A1 | 8/2006 | Vaitekunas |
| 2006/0241426 A1 | 10/2006 | Fujii |
| 2009/0030312 A1 | 1/2009 | Hadjicostis |
| 2009/0149753 A1 | 6/2009 | Assaf |
| 2010/0168572 A1 | 7/2010 | Sliwa |
| 2012/0165666 A1 | 6/2012 | Mischa |

OTHER PUBLICATIONS

Diederich, Chris J. et al "Catheter-Based ultrasound Devices and MR Thermal Monitoring for Conformal Prostate Thermal Therapy", 30 Annual Itnernational IEEE EMBS Conf. 2008.

FIG. 9

MEDICAL ULTRASOUND DEVICE WITH TEMPERATURE DETECTION AT DISTAL END

CROSS-REFERENCE TO RELATED APPLICATIONS

This application is a continuation of U.S. application Ser. No. 13/393,857, filed Mar. 2, 2012, which is the U.S. National Phase application under 35 U.S.C. § 371 of International Application No. PCT/IB2010/054153, filed Sep. 15, 2010, which claims the benefit of European Patent Application No. 09170526.9, filed Sep. 17, 2009, each of which is hereby incorporated by reference.

FIELD OF THE INVENTION

The invention relates to a medical ultrasound device, such as a probe or catheter-based device. In particular the invention relates to such devices capable of detecting the temperature at the distal end of the device.

BACKGROUND OF THE INVENTION

Catheter-based surgery is advantageously used in various connections to treat body organs with minimal incision size and clearance of the organs. As an example, cardiac arrhythmias may be treated by various catheter-based ablation techniques to destroy arrhythmogenic parts of the cardiac tissue. Specifically, radio-frequency (RF) ablation, high intensity focused ultrasound (HIFU) or cryo-ablations of the tissue are commonly used.

In connection with the ablation process of cardiac tissue, it is commonly used to monitor the temperature of the probe during the ablation process. Since the probe is in close proximity with the tissue during the ablation process, the probe temperature reflects the tissue temperature. In some devices of the prior art, the ablation profile may be controlled by the temperature, and direct thermal feedback may be used to titrate the ablation energy.

The US patent application no. 2006/0030844 A1 discloses to use a transparent electrode suitable for radiofrequency (RF) ablation of tissue. It is disclosed to cover a transparent material with a conductive coating so that the conductive coating is capable of delivering RF energy to the tissue, while the combined system of transparent material and coating is transparent to radiation from various imaging modalities. Different surface temperature means for measuring the temperature are disclosed. For example, it is disclosed to place a thermocouple on the electrode surface.

The placement of thermocouple on the electrode surface however puts the thermocouple in the field of view. While this may be acceptable for some application, this may not be the case for all applications. Moreover, there is still a need in the art for alternative or improved temperature sensing solutions, suitable for use in connection with catheter-based surgery.

SUMMARY OF THE INVENTION

The inventors of the present invention have realized that thermocouple-based temperature sensing solutions may not be suitable for use in connection with medical devices comprising integrated ultrasound monitoring in the forward looking geometry, since the positioning of the thermocouple may be in the field of view of the acoustic radiation. Consequently it would be advantageous to achieve a temperature sensing solution which is suitable for integration with medical devices comprising integrated ultrasound transducers. In general, the invention preferably seeks to mitigate, alleviate or eliminate one or more of the above mentioned disadvantages singly or in any combination. In particular, it may be seen as an object of the present invention to provide a medical device that solves the above mentioned problems, or other problems, of the prior art.

To better address one or more of these concerns, in a first aspect of the invention a medical ultrasound device is presented that comprising:

an elongated body having a proximal end, a distal end, a distal end region and a length axis along the elongation;

one or more ultrasound transducers for generating acoustic radiation, the one or more ultrasound transducers being positioned in the distal end region, inside the elongated body;

a transmission element positioned in the radiation path of the acoustic radiation, wherein the transmission element is substantially transparent to acoustic radiation;

a controller unit operatively connected to the ultrasound transducer;

wherein the controller unit detects the acoustic path length through the transmission element and determines the temperature at the distal end from the detected acoustic path length.

The invention provides a medical device, such as a catheter or probe, with integrated ultrasound facilities, where the ultrasound radiation can be used for general purposes, as well as for generating a measure of temperature of the transmission element. Since during use, the transmission element will be in close contact with tissue under investigation or treatment, this temperature will be the same as, or close to, the temperature of the tissue. By measuring the temperature of the transmission element, the temperature at the distal end of the medical ultrasound device, and hence the temperature of the tissue under investigation or treatment, can be determined. In an advantageous embodiment, the one or more ultrasound transducers are capable of generating acoustic radiation suitable for monitoring a region of interest simultaneously with, concurrently with or together with detecting the acoustic path length through the transmission element. By basing the detection of the temperature on ultrasound radiation and path length detection through the transmission element, key elements to perform the temperature detection are elements which also may be used for other purposes, and a separate sensor is not needed. The ultrasound transducer(s) may be used for monitoring purposes and a transmission element is always needed in order to couple the acoustic radiation out of the medical device. A compact and cost-effective medical device is therefore provided. Moreover, in devices with a forward looking geometry, a temperature sensor may be provided which does not shadow the acoustic radiation.

In the context of the present invention, monitoring is to be construed broadly. It includes both 1D monitoring, i.e. detecting reflected intensities along the line of sight as well as 2D imaging where an array of transducers are applied to generate a 2D image. In principle also 3D imaging and time resolved imaging may be obtained. In catheter-based monitoring, it is normal to use 1D or 2D monitoring due to space constraints in the distal end region, i.e. in the tip region.

In general, the transmission element should be substantially transparent to acoustic radiation. A number of materials, including various polymer materials, fulfill this. In general any material can be used, as long as the transparency is sufficient to enable clinical use as well as to enable detection of the acoustic path length through the element. In particular, a material with a transparency to acoustic radiation above 50% may be used, such as above 60%, 70%, 80%, 90%, or even above 95%.

The acoustic path length is detected based on detecting reflected acoustic radiation from the transmission element. In an advantageous embodiment, the acoustic path length is detected based on detecting reflected acoustic radiation from a surface of the backside of the transmission element and a surface of the front-side of the transmission element, the acoustic path length may be detected based on detecting a separation of reflection peaks obtained from the surface of the backside of the transmission element and the surface of the front-side of the transmission element. The detection of the acoustic path length may be based on a detection of the time of flight, and changes in time of flight, of radiation emitted from the transducer, reflected from a surface of the transmission element, and detected again by the transducer.

In an advantageous embodiment, the polymer-based body has a change of velocity of the acoustic radiation larger than 0.1% per degree Celsius or larger, such as 0.25% per degree Celsius or even larger.

In an advantageous embodiment, the distal end region further comprises fluid channels which allow delivery of fluid through the elongated body to the distal end region. Typically, saline fluid may be pumped from a reservoir placed at the proximal end to irrigate the area under investigation or treatment.

In an advantageous embodiment, the temperature at the distal end is determined based on a look-up table or a functional relationship between a parameter related to the acoustic path length and the temperature at the distal end. Such relationships can be deduced from laboratory experiments or calibration routines. Use of look-up tables or functional relationships facilitates fast and flexible ways of correlating the measured path length to the temperature during clinical use.

Advantageously, the transmission element comprises a treatment modality for treatment of body tissue. In an embodiment, the treatment modality is ablation, such as radiofrequency (RF) ablation.

In an embodiment the ablation is performed by use of an electrode supported by the transmission element. The electrode may be provided such that the acoustic radiation is substantially unaffected by the presence of the electrode. In an embodiment, the electrode is in the form of a thin layer sufficiently thin to be substantially transparent to acoustic radiation. Acoustic radiation will be transmitted substantially unaffected by the presence of a metal layer with a thickness below 500 nanometers, such as below 250 nanometers, such as with a thickness of 150 nanometers. In other embodiments, the electrode may be in the form of a mesh or other open structures. An electrode in the form of a mesh, with a central aperture or even in the form of a band or ring, may allow radiation to pass, and still be able to work as an RF-electrode.

In a second aspect of the invention, a method of operating a medical device is presented. A medical device in accordance with the first aspect of the invention is operated by steps which comprise:
  generate acoustic radiation by operating the one or more transducers in a generation mode;
  detect reflected acoustic radiation by operating the one or more transducers in a detection mode;
  from the reflected acoustic radiation detect the acoustic path length of the acoustic radiation through the transmission element;
  determine the temperature at the distal end from the detected acoustic path length.

In a third aspect of the invention, a computer program product is presented that is adapted to enable a computer system comprising at least one computer having data storage means associated therewith to operate a medical device according to according to the first aspects of the invention or to carry out the steps of the second aspect of the invention.

In general the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which
  FIG. 1 schematically illustrates the distal end region of an ablation catheter-based probe.

DESCRIPTION OF EMBODIMENTS

The present invention is disclosed in connection with a RF ablation catheter comprising a monitoring system in accordance with embodiments of the present invention. It is however to be understood that, while such an application is advantageous, the invention is not limited to this. In fact, the medical device may be applied in connection with any device which uses ultrasound transducers and which supports a structural configuration which enables to detect an acoustic path length through a transmission element.

Figure 1:
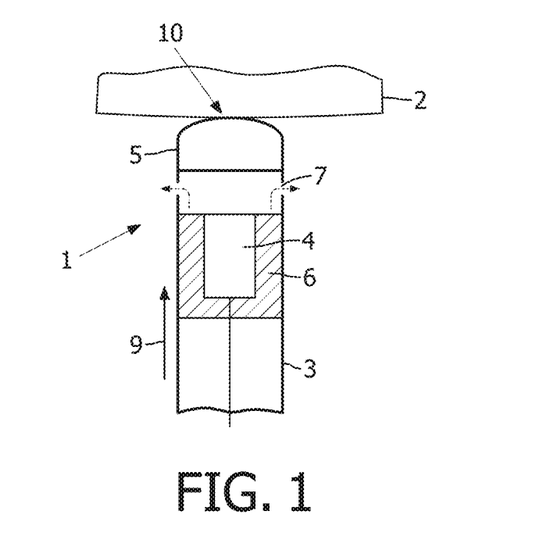

FIG. 1 schematically illustrates the distal end region 1 of an ablation catheter-based probe, hereafter also simply referred to as a catheter. The catheter comprises an elongated body 3, a proximal end (not shown), a distal end 10 and a distal end region 1. A length axis 9 runs along the elongation of the elongated body. The distal end region 1 is the extended end section of the elongated body 3 abutting the distal end itself 10. The catheter may at the proximal end comprise a controller unit or connection for a controller unit (cf. FIG. 9). The ultrasound transducer 4 is housed in the distal end region, where it is fixed by suitable means 6. The catheter comprises a transmission element 5 positioned in the radiation path of the acoustic radiation. The transmission element may be used as transmission window for coupling the acoustic radiation out of the medical device. The transmission element has a backside generally facing the ultrasound transducer and an opposite facing front-side. The transmission element is substantially transparent to acoustic radiation, so that radiation generated by the ultrasound transducer will be transmitted through the transmission element to interact with tissue 2 under investigation or treatment. In an embodiment, the acoustic radiation is emitted along the length axis 9.

As is illustrated in FIG. 1, the distal end region may further comprise fluid channels 7 which allow delivery of fluid through the elongated body to the distal end region so as to irrigate the treatment site during treatment if this is necessary or desirable, typically by use of saline fluid. The fluid channels may be holes into the side of the tube as in the illustrated embodiment, or made by other suitable means.

In an embodiment the device may e.g. be an ultrasound catheter with an integrated ablation electrode. The ultrasound catheter supports monitoring of tissue properties by operating the ultrasound transducer in a monitoring mode, where ultrasound pulses are emitted and the reflected radiation is detected in order to generate an ultrasound image or scan. Operating an ultrasound transducer for detecting reflected radiation is known to the skilled person.

The elongated body may be of a flexible material, such as a suitable polymer material for use in connection with a medical device. Such materials are known to the skilled person. A flexible device is thereby obtained. Alternatively may the elongated body be made of a rigid material, such as surgical steel or other suitable materials as are known to the skilled person. A rigid device may e.g. be implemented as a needle device.

Figure 2:
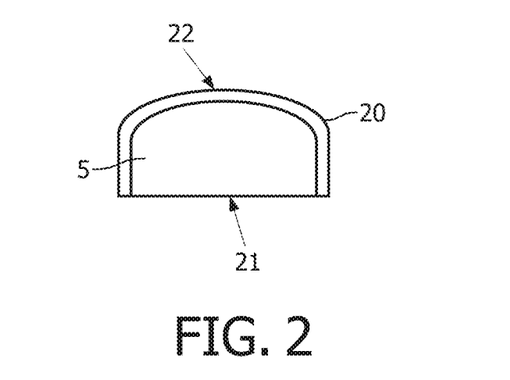
FIG. 2 schematically illustrates an ablation electrode supported by a transmission element.

FIG. 2 schematically illustrates an ablation electrode 20 supported by a transmission element 5. The transmission element has a backside 21 and a front side 22. The ablation electrode may be formed by a thin conducting layer supported by the transmission element. In an embodiment, the transmission element comprises a polymer-based body and a conducting layer. The polymer-based body may be of the material poly-methylpentene (TPX) which is commonly used in connection with ultrasound, whereas the conducting layer may be a metallic layer, such as a platinum layer. Suitable thicknesses may be a few hundred micrometers thick TPX supporting a few hundred nanometer thick platinum layer, such as a 250 micrometer thick TPX element, supporting a 150 nanometer thick platinum layer. The thickness of the TPX element is the thickness at the central region. Other materials may also be used, as long as they are sufficiently transparent to acoustic radiation. The transmission element and supported electrode are illustrated in a rounded configuration which is the clinically relevant shape. In general any shape may be used.

Figure 3:
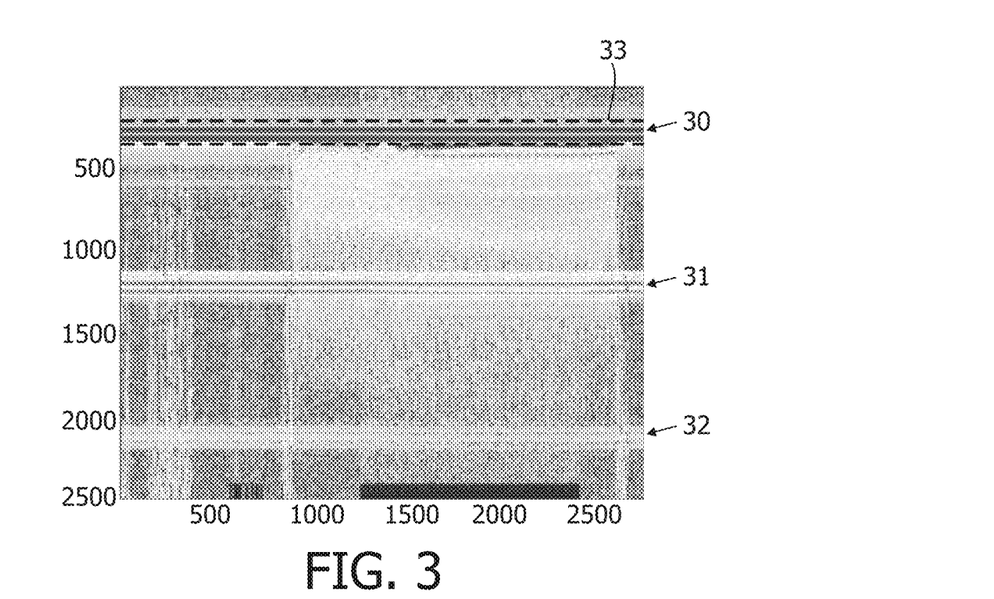
FIG. 3 illustrates a screen shot of an M-mode ultrasound image of cardiac ablation in a sheep heart.

FIG. 3 illustrates a screen shot of an M-mode ultrasound image of cardiac ablation in a sheep heart as generated by an ablation catheter of the type schematically illustrated in FIG. 1. The vertical axis shows the distance from the transducer. The distance is given in pixels which can be converted into time or depth. The horizontal axis illustrates time, again given in pixels (increments of 20 pixels equals 1 second). The image shows the strong primary reflection 30 from the TPX/Pt ablation electrode, and in addition 2nd and 3rd order reflection peaks 31, 32.

Figure 4:
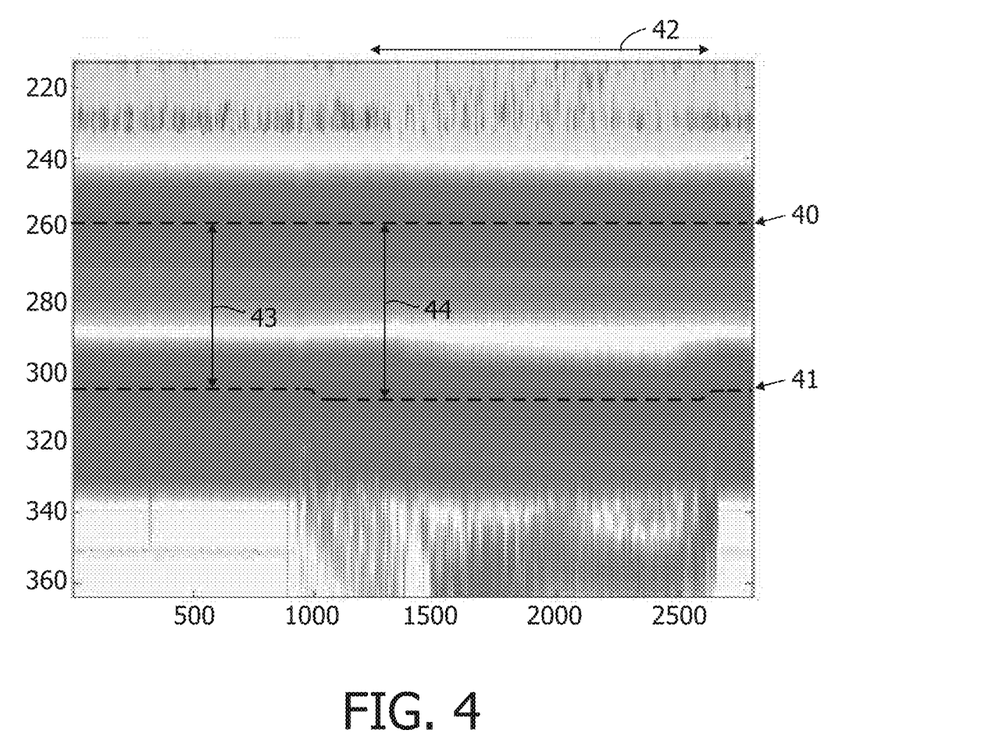
FIG. 4 illustrates a zoom made of the first order TPX/Pt reflection peak of the M-mode image of FIG. 3.

FIG. 4 illustrates a zoom made of the first TPX/Pt reflection peak 30, as indicated with reference numeral 33 on FIG. 3. In FIG. 4, it can be seen that the two peaks (maxima indicated by reference numerals 40, 41) are observed. The positions of these reflections are related to the time-of-flight of the ultrasound signal, and therefore the acoustic path length through the transmission element. The maxima of the two peaks are observed to be relatively constant with respect to time in the first half of the image, however as can be seen during the period indicated with reference numeral 42 where the ablation process is running, the distance 43, 44 between the two peaks increases. The first peak 40 corresponds to the transition of the acoustic radiation into the transmission element, and the second peak 41 corresponds to the transition of the acoustic radiation out of the transmission element. In the area between the two peaks, the ultrasound radiation is propagating inside the transmission element. Due to the ablative process, the temperature of the ablation electrode and the tissue increases and as a result, the acoustical path length through the transparent ablation electrode increases too. By monitoring the positioning of the two peaks, the acoustic path length can be monitored. From analysis of the monitored data, it is possible to obtain sub-pixel resolution. The main physical effect which gives rise to the changes in the acoustical path length is the change of the speed of sound in dependence upon the temperature changes. It can be mentioned that the material expansion of either the electrode or the transmission element over the relevant temperature ranges is nearly negligible. As the temperature rises, the speed of sound decreases, resulting in an increases acoustical path length, which is seen as an increase in the distance 43, 44 between the two peaks.

Figure 5:
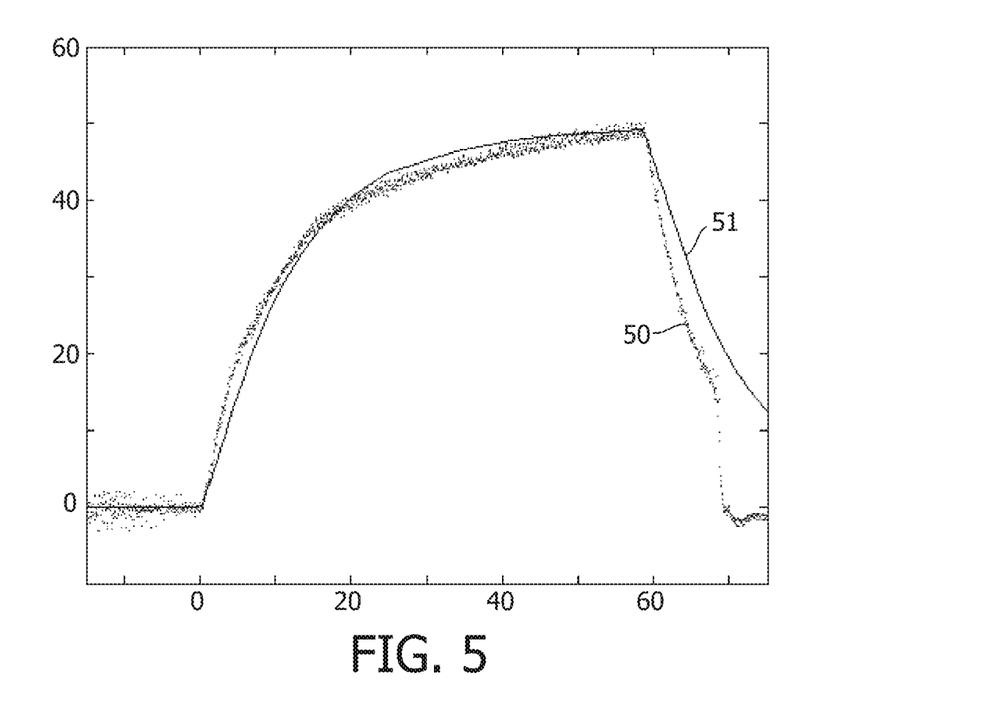
FIG. 5 shows a graph of peak separation as a function of time.

FIG. 5 shows a graph of the peak separation 43, 44 as a function of time in the ablation period as indicated with reference numeral 42 in FIG. 4. The vertical axis is peak separation in pixels and the horizontal axis is time in seconds. The graph shows measuring points 50 as well as a calculated line 51 of the expected thermal effect. The calculation was obtained by assuming 4 mm thick cardiac tissue, cold surfaces and a 6 mm diameter ablation catheter. The vertical axis includes only a single fitting parameter in the form of the product of the ablation power and thermal conductivity. The horizontal axis does not contain fitting parameters. As can be seen, during the ablation process, the acoustical path length through the transmission element clearly increases. Subsequently, at the end of the ablation (at time=60 sec.) a rapid cooling is observed. The final jump at time=70 sec. is due to removal of the device from the heart wall.

Figure 6:
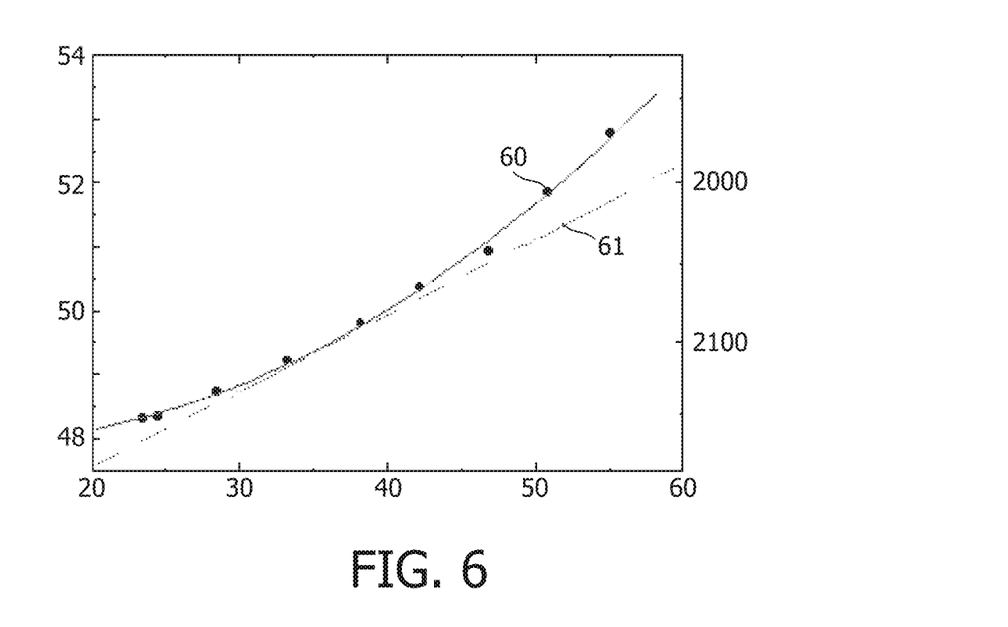
FIG. 6 illustrates a graph correlating the peak separation, the speed of sound and the temperature.

FIG. 6 illustrates a graph correlating the peak separation (left vertical axis), the speed of sound (right vertical axis) and the temperature in degree Celsius (horizontal axis). The measurement points are shown as solid bullets 60 (a line is drawn through the points to guide the eye), moreover, a line 61 is shown indicating 0.25% expansion per ° C. of the acoustic path length for comparison to the data. As can be seen the catheter is capable of accurately determining the temperature at the location of the point of contact between the ablation electrode and the tissue, which is the clinically interesting point.

Figure 7:
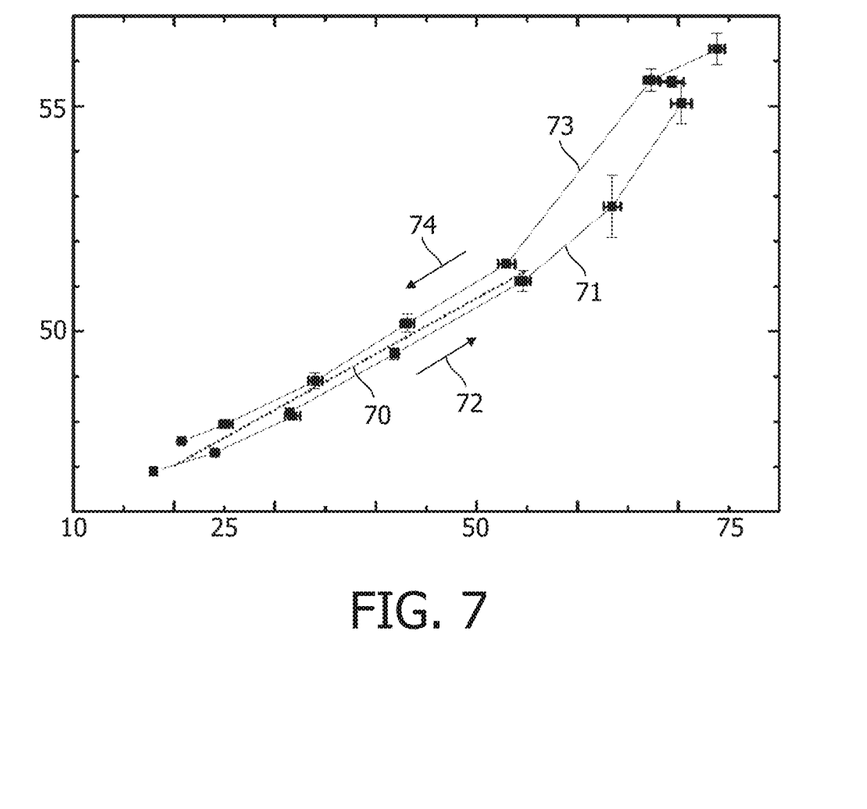
FIG. 7 further illustrates peak separations as a function of temperature.

FIG. 7 further illustrates peak separations as a function of temperature. FIG. 7 illustrates a laboratory experiment, where the acoustical path length between the two peaks was measured for a medical device with the distal end region submerged in a water bath for a series of constant temperatures. A line 70 is shown which indicate 0.25% expansion per ° C. of the acoustic path length for comparison to the data. Point connected by the line with reference numeral 71 connect data points obtained during temperature rise 72, whereas point connected by the line with reference numeral 73 connect data points obtained during temperature decent 74. As can be seen, thermal resolution is of the order of 1° C. within the range of clinical relevant temperatures.

In a situation of use, the temperature at the distal end may be determined based on a look-up table or a functional relationship between a parameter related to the acoustic path length and the temperature at the distal end, e.g. as deduced from a measurement as presented in FIG. 7. Look-up table, functional relationships etc. may be stored by and computed in the controller unit or a computing unit in or connected to the controller unit.

Figure 8:
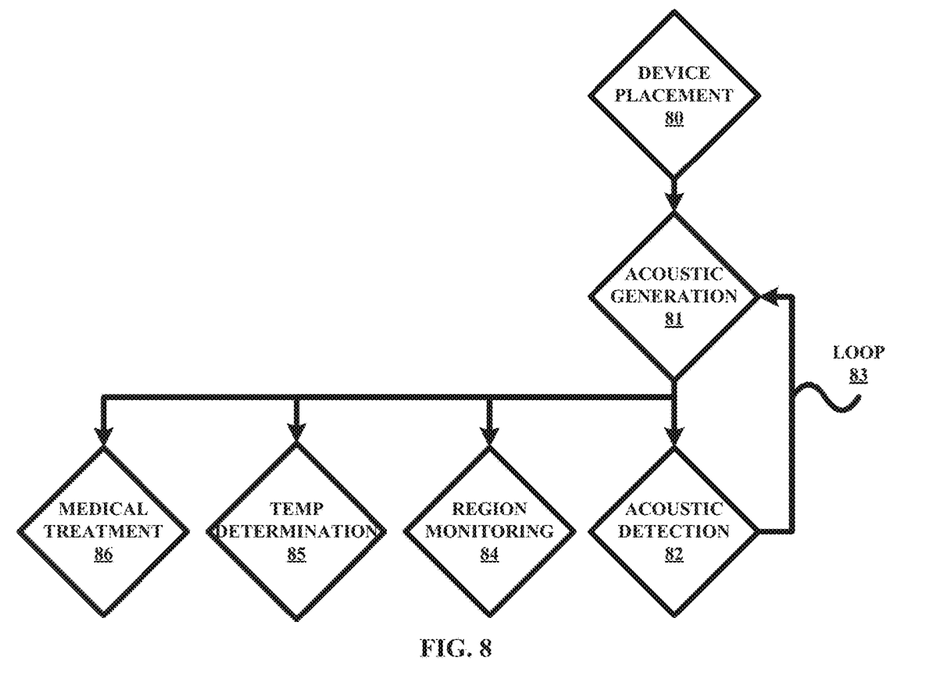
FIG. 8 illustrates a flow diagram of steps performed in connection operating a medical device.

FIG. 8 illustrates a flow diagram of some of the steps which may be performed in order to operate a medical device in accordance with embodiments of the present invention. Firstly, the medical device may be positioned 80 in the region of interest, for example in close proximity of cardiac tissue to undergo ablation treatment. The transducers are operated to generate 81 acoustic radiation and to detect 82 the reflected acoustic radiation. The transducers may be operated continuously 83 during the investigation and treatment. The reflected acoustic radiation is detected in order to monitor 84 the region of interest during the procedure, and from the reflected acoustic radiation also the acoustic path length is deduced to determine the temperature 85 at the distal end. Simultaneously with the monitoring and the temperature detection, the treatment modality may be operated 86 in order to perform medical treatment. For example, the tissue under treatment may undergo ablation.

Figure 9:
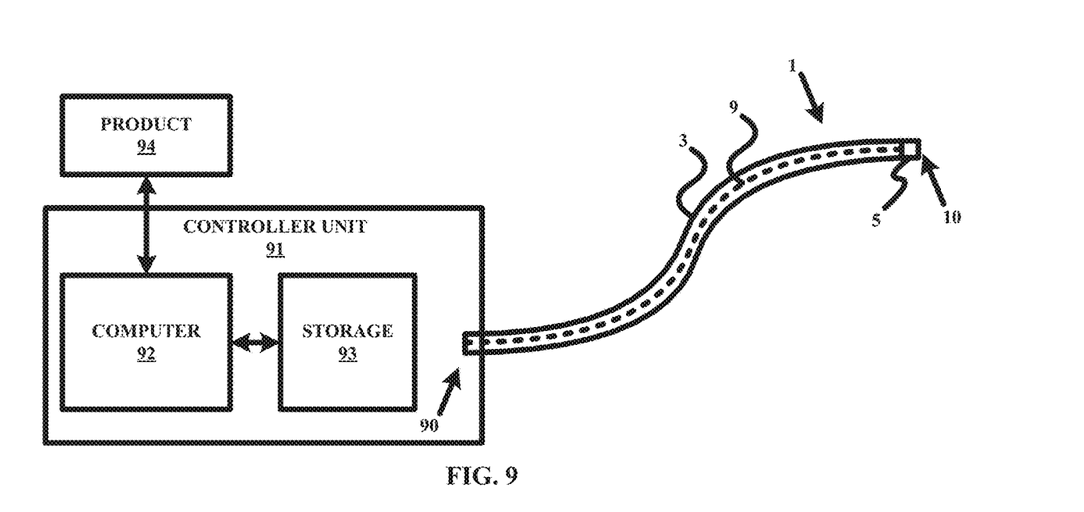
FIG. 9 schematically illustrates a medical device connected to a controller unit and in connection with a computer program product.

FIG. 9 schematically illustrates a medical device connected to a controller unit and in connection with a computer program product. The medical device comprises a catheter in accordance with embodiments of the present invention. The catheter comprises an elongated body 3 having a proximal end 90, a distal end 10, a distal end region 1 and a length axis 9 along the elongation. Moreover, the catheter comprises one or more ultrasound transducers positioned in the distal end region and a transmission element 5 positioned at the extremity of the elongated body to couple acoustic radiation in and out of the catheter.

The catheter is at the proximal end 90 connected to a controller unit 91, such as a dedicated purpose or general purpose computing unit for control of at least the ultrasound transducer(s) and for dealing with the signal treatment and extraction of detection results. To this end, the detection of the acoustic path length through the transmission element and the determination of the temperature at the distal end are controlled by the controller unit 91.

The controller unit may implement a computer system 92, such as a dedicated purpose or general purpose computing unit for controlling the device. The computer system may comprise storage means 93 for storing data which may be needed to operate the medical device or to store any acquired data, or for any other purpose where storage of data is desired. The computer system may be adapted to receive instructions from a computer program product 94 in order to operate the device. The computer program product may be comprised in a data carrier as illustrated in the Figure, however once loaded into the computer system it may be stored by, and run from, the storage means 93.

In the foregoing, simultaneous operation of the monitoring, the ablation and the temperature sensing have been described. While it is an advantage of embodiments of the present invention that such simultaneous operation is feasible, also interleaved operation of one or more of the operation modalities is possible if this is desired.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

What is claimed is:

1. An ultrasonic temperature determination device, comprising:
    a controller unit configured to be coupled to an ultrasound imaging device comprising an ultrasound transducer coupled to a distal region of an elongate body, the controller unit configured to:
        control the ultrasound transducer of the ultrasound imaging device to emit acoustic radiation through a transmission element coupled to the elongate body at a fixed position relative to the ultrasound transducer;
        receive an ultrasound signal from the ultrasound transducer, wherein the ultrasound signal is representative of reflections of the acoustic radiation from a surface of a backside and a surface of a front-side of the transmission element;
        determine, based on the ultrasound signal, an acoustic path length between the surface of the backside and the surface of the front-side of the transmission element; and
        determine a temperature of the transmission element based on the acoustic path length.

2. The device of claim 1, wherein the controller unit is configured to determine the acoustic path length by detecting a separation of reflection peaks from the surface of the backside and the surface of the front-side of the transmission element.

3. The device of claim 1, wherein the controller unit is configured to determine the temperature of the transmission element based on a look-up table or a functional relationship between a parameter related to the acoustic path length and temperatures of the transmission element.

4. The device of claim 1, wherein the controller unit is configured to:
    generate M-mode imaging data based on the ultrasound signal; and
    determine the acoustic path length based on the M-mode imaging data.

5. The device of claim 1, wherein the controller unit is further configured to control an ablation electrode of the ultrasound imaging device coupled to the distal region of the elongate body to emit ablation energy into a tissue of a patient.

6. The device of claim 5, wherein the controller unit is configured to simultaneously control the ablation electrode to emit the ablation energy and the ultrasound transducer to emit the acoustic radiation.

7. The device of claim 6, further comprising the ultrasound imaging device.

8. The device of claim 7, wherein the ablation electrode is disposed on a distal surface of the transmission element.

9. The device of claim 8, wherein the ablation electrode comprises a metallic layer.

10. The device of claim 7, wherein the transmission element comprises an acoustically transparent polymer-based body.

11. The device of claim 10, wherein the acoustically transparent polymer-based body is configured such that a velocity of the acoustic radiation changes more than 0.1% per degree Celsius.

12. The device of claim 7, wherein the transmission element is spaced from the ultrasound transducer.

13. The device of claim 12, wherein the elongate body includes fluid channels that allow delivery of a fluid to the distal region.

14. The device of claim 13, wherein the fluid channels are configured to deliver the fluid into a space between the ultrasound transducer and the transmission element.

\* \* \* \* \*